US008620409B2

United States Patent
Sachse et al.

(10) Patent No.: US 8,620,409 B2
(45) Date of Patent: Dec. 31, 2013

(54) DYE APPLICATION FOR CONFOCAL IMAGING OF CELLULAR MICROSTRUCTURE

(75) Inventors: Frank B. Sachse, Salt Lake City, UT (US); John H. Bridge, Salt Lake City, UT (US); Robert Hitchcock, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 235 days.

(21) Appl. No.: 13/057,419

(22) PCT Filed: Aug. 4, 2009

(86) PCT No.: PCT/US2009/004457
§ 371 (c)(1),
(2), (4) Date: Aug. 25, 2011

(87) PCT Pub. No.: WO2010/016885
PCT Pub. Date: Feb. 11, 2010

(65) Prior Publication Data
US 2011/0301438 A1 Dec. 8, 2011

Related U.S. Application Data

(60) Provisional application No. 61/137,876, filed on Aug. 4, 2008.

(51) Int. Cl.
*A61B 5/00* (2006.01)
(52) U.S. Cl.
USPC ............ 600/428; 600/431; 600/478; 424/9.6; 424/9.61

(58) Field of Classification Search
USPC ................. 600/407, 425, 428, 431, 476–478; 424/9.6, 9.61
See application file for complete search history.

(56) References Cited

U.S. PATENT DOCUMENTS 5,298,741 A * 3/1994 Walt et al. ................. 250/227.23
6,110,106 A * 8/2000 MacKinnon et al. ......... 600/181
(Continued)

FOREIGN PATENT DOCUMENTS

| CA | 2732962 | 2/2010 |
|---|---|---|
| EP | 2324362 | 5/2011 |
| JP | 2011-530082 | 12/2011 |
| WO | WO 2010/016885 | 2/2010 |

OTHER PUBLICATIONS

PCT/US2013/22247, University of Utah Research Foundation, English.
(Continued)

*Primary Examiner* — Ruth S Smith
(74) *Attorney, Agent, or Firm* — Ballard Spahr LLP

(57) ABSTRACT

A system and method for confocal imaging of tissue in vivo and in situ, e.g., for minimally invasive diagnosis of patients. A catheter is provided that has a dye carrier coupled to the distal end of a fiber optics bundle, which allows for the introduction of at least one fluorescent dye therein the dye carrier into a portion of the tissue of interest of a subject or patient when the dye carrier is selectively brought into contact with the portion of the tissue of interest. The resulting confocal images permit the acquisition of diagnostic information on the progression of diseases at cellular/tissue level in patients. Furthermore, a system for ECG-triggered image acquisition is provided.

30 Claims, 12 Drawing Sheets

(56) References Cited

U.S. PATENT DOCUMENTS

| | | | |
|---|---|---|---|
| 6,134,003 | A | 10/2000 | Tearney |
| 6,413,252 | B1 | 7/2002 | Zavislan |
| 6,522,444 | B2 | 2/2003 | Mandella |
| 6,627,177 | B2 | 9/2003 | Singaram |
| 6,889,075 | B2 | 5/2005 | Marchitto |
| 6,911,216 | B1 | 6/2005 | Roth |
| 7,190,990 | B2 | 3/2007 | Zavislan |
| 7,221,824 | B2 | 5/2007 | Berier |
| 7,225,010 | B1 | 5/2007 | Zavislan |
| 7,285,089 | B2 | 10/2007 | Viellerobe |
| 8,383,415 | B2 * | 2/2013 | Ayi et al. ............ 436/172 |
| 2003/0028099 | A1 * | 2/2003 | Thorn Leeson et al. ...... 600/431 |
| 2004/0242469 | A1 | 12/2004 | Lee |
| 2005/0119523 | A1 | 6/2005 | Starksen |
| 2005/0157981 | A1 * | 7/2005 | Berier et al. ............ 385/33 |
| 2005/0242298 | A1 | 11/2005 | Genet |
| 2007/0135776 | A1 * | 6/2007 | Yamamoto et al. ........... 604/289 |
| 2007/0149851 | A1 * | 6/2007 | Nakamura et al. ........... 600/129 |
| 2007/0173718 | A1 * | 7/2007 | Richards-Kortum et al. 600/431 |
| 2007/0293721 | A1 * | 12/2007 | Gilboa ............ 600/117 |
| 2008/0004495 | A1 * | 1/2008 | Allen et al. ............ 600/160 |
| 2008/0243002 | A1 * | 10/2008 | Munce et al. ............ 600/459 |
| 2011/0301438 | A1 | 12/2011 | Sachse |

OTHER PUBLICATIONS

Andries LJ, et al. (1994) Endocardial endothelium in the rat: junctional organization and permeability. Cell Tissue Res., 277(3): 392-400.

Ayres CE, et al. (2008) Measuring fiber alignment in electrospun scaffolds: a user's guide to the 2D fast Fourier transform approach. J Biomater Sci Polym Ed., 19(5):603-621.

Cheng H, et al. (1999) Amplitude Distribution of calcium Sparks in Confocal Images: Theory and Studies with an Automatic Detection Method. Biophysical Journal: 606-617.

Engelmayr GC Jr, et al. (2008) Accordion-like honeycombs for tissue engineering of cardiac anisotropy. Nat Mater., 12: 1003-1010.

Ghosh KK, et al. (2011) Miniaturized integration of a fluorescence microscope. Nature Methods, 8(10): 871-878.

Lasher RA, et al. Microstructural Comparison of Engineered and Native Cardiac Tissue Based on Three-Dimensional Confocal Microscopy. Tissue Engineering, 1-52.

Lasher RA, et al. (2009) Towards modeling of cardiac micro-structure with catheter-based confocal microscopy: a novel approach for dye delivery and tissue characterization. IEEE Trans Med Imaging, 28(8):1156-1164.

Lucy LB, et al. (1974) An iterative technique for the rectification of observed distributions. *Astronomical Journal*, 79:745.

Nichol JW, et al. (2008). Co-culture induces alignment in engineered cardiac constructs via MMP-2 expression. Biochem Biophys Res Commun, 373(3):360-365.

Richardson WH. (1972) Bayesian-based iterative method of image restoration. J. Opt. Soc. Am., 62:55-59.

Rouse AR, et al. (2004) Design and demonstration of a miniature catheter for a confocal microendoscope. Applied Optics,43(31): 5763-5771.

Sachse FB, et al. (2012) Subcellular structures and function of myocytes impaired during heart failure are restored by cardiac resynchronization therapy. Circ. Res. AHA, 110(4):588-597.

Sachse FB, et al. (2009) Towards computational modeling of excitation-contraction coupling in cardiac myocytes: reconstruction of structures and proteins from confocal imaging. Pac Symp Biocomput, 328-339.

Savio E, et al. (2007) A framework for analyzing confocal images of transversal tubules in cardiomyocytes. Lect Notes Comput Sci., 4466: 110-119.

Savio-Galimberti E, et al. (2008) Novel features of the rabbit transverse tubular system revealed by quantitative analysis of three-dimensional reconstructions from confocal images. Biophys J., 95(4):2053-2062.

Sung KB, et al. (2003) Fiber optic confocal reflectance microscopy: a new real-time technique to view nuclear morphology in cervical squamous epithelium in vivo. Opt Express, 11(24):3171-3181.

Sung KB, et al. (2002) Fiber-optic confocal reflectance microscope with miniature objective for in vivo imaging of human tissues. IEEE Trans Biomed Eng., 49(10):1168-1172.

International Preliminary Report on Patentability issued by the International Bureau on Feb. 8, 2011 for PCT/US2009/004457 filed on Aug. 4, 2009 and published as WO 2010/016885 on Nov. 2, 2010 (Applicant—University of Utah Research Foundation // Inventors—Sachse et al.) (8 pages).

International Search Report and Written Opinion mailed by the International Bureau on Dec. 28, 2009 for PCT/US2009/04457 filed on Aug. 4, 2009 and published as WO 2010/016885 on Nov. 2, 2010 (Applicant—University of Utah Research Foundation// Inventors—Sachse et al.) (9 pages).

Amended Claims filed with the European Patent Office on Apr. 21, 2011 for European patent application 09805257.4 which claims priority to PCT/US2009/004457 filed Aug. 4, 2009 (Applicant—University of Utah Research Foundation // Inventors—Sachse et al.) (17 pages).

* cited by examiner time

DYE APPLICATION FOR CONFOCAL IMAGING OF CELLULAR MICROSTRUCTURE

CONTINUITY

This application is a National Phase Application of International Application No. PCT/US2009/004457, filed Aug. 4, 2009, which claims priority to U.S. Patent Application No. 61/137,876, filed Aug. 4, 2008, which applications are incorporated herein fully by this reference.

FIELD OF THE INVENTION

This invention generally relates to diagnosis of a large class of diseases, which affect the microstructure of tissues, the size and shape of cells, and the arrangement of cells. Alterations of tissues and cells have been reported for cardiac diseases, e.g., hypertrophy, infarction and ischemia, which are the leading cause of death in most developed countries.

BACKGROUND

Currently, magnetic resonance (MR), ultrasonic (US) and computer tomographic (CT) imaging techniques are major tools for clinical diagnosis of diseases and evaluation of therapeutic interventions. Confocal microscopic imaging techniques constitute a state-of-the-art approach to study progression of diseases in ex vivo preparations of tissue and cells of animal models and to evaluate potential treatments, including stem cells, pharmaceuticals and device implants.

Confocal microscopy is an indispensable tool in cell biology because the optical sectioning ability of confocal microscopic imaging enables the study of molecular and morphologic changes in thick biologic specimens with sub-micrometer resolution. Typically, confocal microscopy has not been used to examine living tissue because of the need for close association between microscope instrumentation and the imaged tissue, toxic or expensive fluorescent dyes for image contrast, and relatively long image acquisition times. Despite these challenges, confocal microscopy techniques have been shown to provide valuable diagnostic information for various disease states. Studies with biopsy specimens suggest that confocal imaging can provide useful diagnostic information about the presence of precancerous lesions; confocal images of normal and dysplastic cervical biopsy specimens obtained with a confocal reflectance microscope showed a strong correlation between nuclear morphologic features extracted from confocal images and histopathologic diagnosis.

Confocal microscopic imaging techniques create high resolution images and differs from conventional optical microscopy in that it uses a condenser lens to focus illuminating light of specific wavelengths from a light source, e.g. laser, into a very small, diffraction limited spot within a specimen, and an objective lens to focus the light emitted from that spot onto a small pinhole in an opaque screen. A detector, which is capable of quantifying the intensity of the light that passes through the pinhole at any instant, is located behind the screen. Because only light from within the illuminated spot is properly focused to pass through the pinhole and reach the detector, any stray light from structures above, below, or to the side of the illuminated spot are filtered out. The image resolution is therefore greatly enhanced as compared to other conventional approaches.

In a scanning confocal microscopic imaging system, a coherent image is built up by scanning point by point over the desired field of view and recording the intensity of the light emitted from each spot, as small spots are illuminated at any one time. Scanning can be accomplished in several ways, including for example and without limitation, via laser scanning. Confocal microscopic imaging system are commercially available through entities such as Carl Zeiss, Nikon, and Olympus. An exemplary confocal is described in U.S. Pat. No. 6,522,444 entitled "Integrated Angled-Dual-Axis Confocal Scanning Endoscopes," which is assigned to Optical Biopsy Technologies Inc.

The ability to obtain confocal images of normal and diseased tissue in vivo is limited by the ability to bring the tissue of interest in close proximity to the microscope objective. Flexible confocal microscopic imaging systems incorporating either a solitary optical fiber or a fiber optic imaging bundle are needed to facilitate in vivo imaging of less accessible organ sites. However, a major obstacle for application of confocal microscopic imaging techniques is related to the introduction of fluorescent dyes into biological tissue. Commonly, introduction of dye is performed by infusion or systemic needle injection. Disadvantages of these methods include, for example, the high dosing requirements, washout and inhomogeneous distribution of the fluorescent dye.

SUMMARY OF THE INVENTION

The present invention relates to a catheter that is configured for the use with a confocal microscopic imaging system including conventional and those based on fiber-optics. The catheter is adapted for the study of tissue at locations within a body wherein one or more fluorescent dyes are selectively introduced into the tissue region under observation.

In one embodiment, the catheter system comprises a fiber-optic bundle disposed therein at least a portion of a catheter sheath and a carrier of fluorescent dye that is operatively coupled to a distal end of the fiber-optic bundle. In one exemplary aspect, the carrier of fluorescent dye can comprise one or more fluorescent dyes that are loaded therein the carrier at a predetermined concentration and weight per volume of the carrier. The proximal end of the fiber-optic bundle is operatively coupled to a confocal microscopic imaging system, as known in the art and as exemplarily described above.

In operation, the distal end portion of the catheter is steered through blood vessels or body cavities to a location adjacent to a tissue of interest. Subsequently, the dye carrier is brought in contact with the desired vessel or cavity surfaces, respectively. After contact of the dye carrier with the surfaces, the fluorescent dye(s) are allowed to diffuse from the dye carrier into the tissue. The fluorescent dye is then excited by a light source, such as a focused laser beam, of appropriate wavelength to emit light of a different wavelength for transmission through the fiber optics bundle of the catheter. As one will appreciate, scanning through tissue by exciting the dye and measuring intensities of emitted light allows for two- and three-dimensional imaging.

According to one embodiment, a method for producing an image of a tissue comprises generating light at a desired wavelength, transmitting the light into a fiber-optic bundle toward a distal end of the fiber-optic bundle and through the dye carrier onto a portion of the tissue of the subject that has been introduced with the one or more fluorescent dyes to excite the fluorescent dye therein the selected tissue. Subsequently, light of a different wavelength is emitted by the excited fluorescent dye and is received therethrough the dye carrier and into the distal end of the fiber-optic bundle, which is operatively coupled to a confocal microscopic system. From the measured intensities of emitted light, two-dimensional images of the tissue and stacks of those images are acquired with imaging techniques in the confocal microscopic system.

According to another embodiment, a method for producing an ECG-triggered image is described, wherein a reference point of an ECG signal taken from the subject triggers initiates each image acquisition. The imaging comprises generating light at a desired wavelength, repeatedly transmitting the light into a tissue at a desired location within the subject, receiving emitted light from the excited fluorescent dye at the desired location as a result of each light transmission, and processing the received emitted light to form an image or image stack. In one exemplary aspect, a high resolution fast multi-spectral confocal mapping technique and apparatus can be used.

Other apparatus, methods, and aspects and advantages of the invention will be discussed with reference to the figures and to the detailed description of the preferred embodiments.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

DETAILED DESCRIPTION OF THE INVENTION

Figure 1:
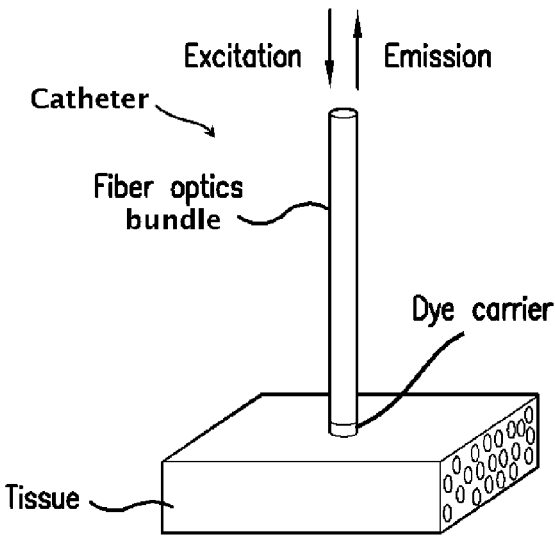
FIG. 1 shows a schematic view of an embodiment of a catheter having a catheter sheath, a fiber-optic bundle, and a dye carrier coupled to a distal end of the fiber-optic bundle. In operation, the dye carrier positioned in contact with a tissue of interest allows dye to diffuse from the dye carrier into portions of the tissue of interest.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a dye," can include two or more such dyes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject can include humans and can also include small or laboratory animals as well as primates. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

As used herein and without limitation, "tissue" can refer to an aggregate of cells of a particular kind, together with their intercellular substances, that forms a solid or fluid material. In one aspect, at least one portion of the tissue of interest must be accessible to the device. In one exemplary non-limiting aspect, the tissue can be cardiac tissue. Other tissues suitable for use with this invention include pulmonary, gastrointestinal, urogynecologic, endocrine, neural or vascular tissue.

Figure 2:
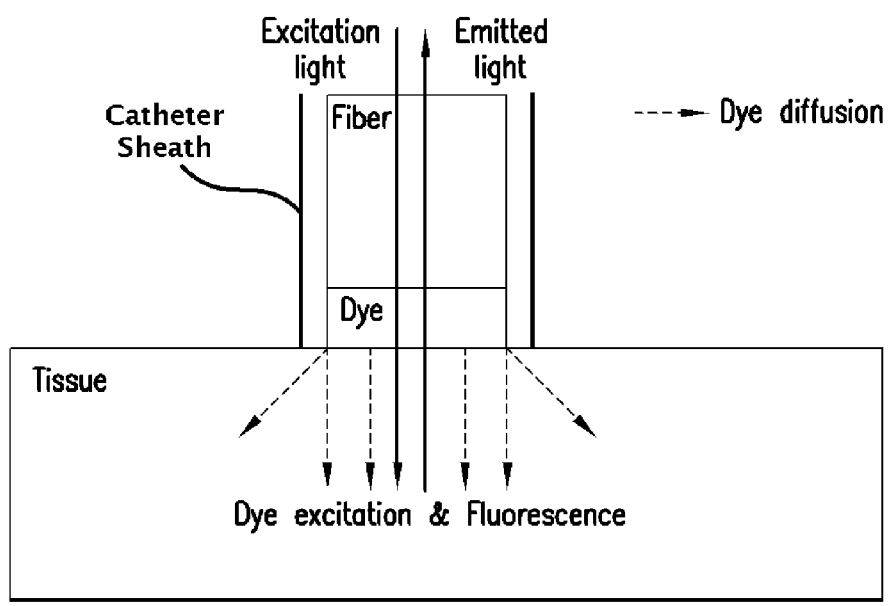
FIG. 2 shows a schematic view of the principle of dye injection and imaging. Diffusion underlies the release of dye from the carrier and dye transport in the tissue of interest. Excitation and emitted light is transmitted through the fiber-optic bundle and the dye carrier.

Referring to FIGS. 1 and 2, in one embodiment, a catheter is provided for use with a conventional confocal microscopic imaging system that is configured to develop a confocal image of a portion of a desired tissue of a subject. In one aspect, and as described in more detail below, the confocal microscopic imaging system can comprise a processor. In a further aspect, the catheter can comprise a fiber-optic bundle and a dye carrier.

In one aspect, the fiber-optic bundle has a distal end and an opposed proximal end. In this aspect, the proximal end of the fiber-optic bundle is placed in operable communication with the confocal microscopic imaging system. In a further aspect, the dye carrier comprises at least one fluorescent dye and is operatively coupled to the distal end of the fiber-optic bundle. In yet another aspect, the catheter can include a catheter sheath that is configured to selectively and at least partially enclose a distal end portion of the fiber-optic bundle. It is also contemplated that the catheter sheath can be configured to selectively and at least partially enclose at least a portion of the dye carrier.

In a further aspect, the fiber-optic bundle is in communication with a source of light that is configured for selective generation of light at a desired wavelength. As one skilled in the art will appreciate, this allows for light of selected wavelengths to be selectively transmitted down the fiber-optic bundle and through the dye carrier positioned at the distal end of the fiber-optic bundle. In a further aspect, the catheter can comprise a means for positioning a portion of the dye carrier in contact against a tissue region of interest to selectively diffuse the at least one fluorescent dye into the tissue region of interest. Optionally, it is contemplated that the means for positioning a portion of the dye carrier in contact against a tissue region of interest can comprise a means for steering the catheter sheath within the subject to position the dye carrier against the tissue region of interest.

In another aspect, the dye carrier comprises a light transparent matrix and at least one fluorescent dye. It is further contemplated that the at least one florescent dye can be suspended in a conventional buffer solution such that the at least one florescent dye in its buffer solution can be diffused therein at least a portion of the light transparent matrix of the dye carrier at a predetermined desired concentration. In one example, the at least one fluorescent dye and its buffer solution comprise at least 95% of the dye carrier by weight. In various other exemplary aspects, it is contemplated that the at least one fluorescent dye and its buffer solution can comprise at least 10% of the dye carrier by weight, alternatively, at least 50% of the dye carrier by weight, and, optionally, at least 75% of the dye carrier by weight. In a further aspect, the dye carrier can further comprise at least one conjugated agent, for example and not meant to be limiting, an antibody.

In exemplary aspects, the light transparent matrix can comprise a hydro-gel. In these aspects, it is contemplated that the light transparent matrix can extend from the distal end of the fiber optic bundle for less than 200 µm. It is further contemplated that the light transparent matrix can extend from the distal end of the fiber optic bundle for less than 100 µm. In various experiments, which are not meant to be limiting but rather serve as exemplary examples, the dye carrier was formed from a hydro-gel having a thickness of between about 30 to about 100 µm and that was configured to have an area in contact with the selected portion of the tissue that ranged from between about 1 to about 4 $mm^2$. In these tests, the formed hydro-gel dye carrier comprised about 5% agar and about 95% water.

Prior to application of the formed hydro-gel dye carrier to the tissue region of interest, between about 0.1 to about 0.5 mg of fluorescent dye in its conventional buffer solution was loaded on the hydro-gel dye carrier and was allowed to diffuse into the dye carrier for approximately 1 min. Fluorescent dyes that were tested include dextran conjugated Alexa 488 and dextran conjugated Texas Red (both from Invitrogen).

As one skilled in the art will appreciate, the system and methods described herein rely on fluorescence as an imaging mode, primarily due to the high degree of sensitivity afforded by the confocal imaging technique coupled with the ability to specifically target structural components and dynamic processes in chemically fixed as well as living cells and tissues. Many fluorescent probes have been constructed around synthetic aromatic organic chemicals designed to bind with a biological macromolecule (for example, a protein or nucleic acid) or to localize within a specific structural region, such as the cytoskeleton, mitochondria, Golgi apparatus, endoplasmic reticulum, and nucleus. Other fluorescent probes are employed to monitor dynamic processes and localized environmental variables, including concentrations of inorganic metallic ions, pH, reactive oxygen species, and membrane potential. Fluorescent dyes are also useful in monitoring cellular integrity (live versus dead and apoptosis), endocytosis, exocytosis, membrane fluidity, protein trafficking, signal transduction, and enzymatic activity. Despite the numerous advances made in fluorescent dye synthesis during the past few decades, there is very little solid evidence about molecular design rules for developing new fluorochromes, particularly with regard to matching absorption spectra to available confocal laser excitation wavelengths. As a result, the number of fluorophores that have found widespread use in confocal microscopy is a limited subset of the many thousands that have been discovered.

Fluorophores chosen for confocal applications generally are selected to exhibit a excitability, intensity of emitted lights, and signal persistence sufficient for the instrument to obtain image data that does not suffer from excessive photobleaching artifacts and low signal-to-noise ratios. In widefield fluorescence microscopy, excitation illumination levels are easily controlled with neutral density filters, and the intensity can be reduced (coupled with longer emission signal collection periods) to avoid saturation and curtail irreversible loss of fluorescence. Excitation conditions in confocal microscopy are several orders of magnitude more severe, however, and restrictions imposed by characteristics of the fluorophores and efficiency of the microscope optical system become the dominating factor in determining excitation rate and emission collection strategies.

In confocal microscopy, excitation of the fluorophores with a focused laser beam at high power densities increases the emission intensity up to the point of dye saturation, a condition whose parameters are dictated by the excited state lifetime. In the excited state, fluorophores are unable to absorb another incident photon until they emit a lower-energy photon through the fluorescence process. When the rate of fluorophore excitation exceeds the rate of emission decay, the molecules become saturated and the ground state population decreases. As a result, a majority of the laser energy passes through the specimen undiminished and does not contribute to fluorophore excitation. Balancing fluorophore saturation with laser light intensity levels helps to achieve a desired signal-to-noise ratio in confocal applications.

The number of fluorescent probes currently available for confocal microscopy runs in the hundreds, with many dyes having absorption maxima closely associated with common laser spectral lines. An exact match between a particular laser line and the absorption maximum of a specific probe is not always possible, but the excitation efficiency of lines near the maximum is usually sufficient to produce a level of fluorescence emission that can be readily detected. For example, in FIG. 7 the absorption spectra of two common probes are illustrated, along with the most efficient laser excitation lines. The green spectrum is the absorption profile of fluorescein isothiocyanate (FITC), which has an absorption maximum of 495 nanometers. Excitation of the FITC fluorophore at 488 nanometers using an argon-ion laser produces an emission efficiency of approximately 87 percent. In contrast, when the 477-nanometer or the 514-nanometer argon-ion laser lines are used to excite FITC, the emission efficiency drops to only 58 or 28 percent, respectively. One skilled in the art will appreciate that, in this example, the 488-nanometer argon-ion (or krypton-argon) laser line is the most efficient source for excitation of this fluorophore.

Figure 7:
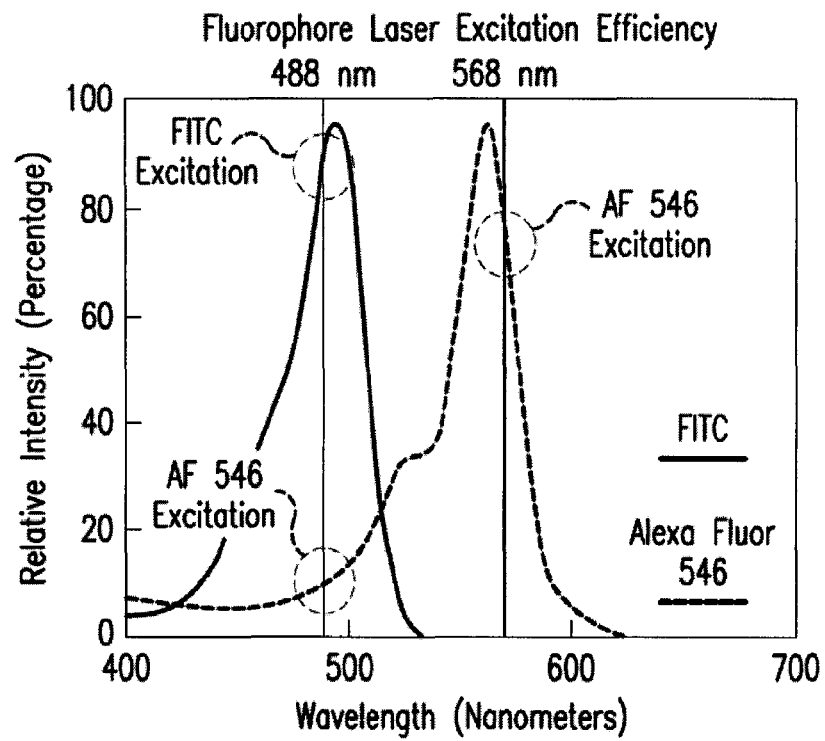
FIG. 7 shows the absorption profile of fluorescein isothiocyanate (FITC) in green and the absorption profile of Alexa Fluor 546 in red.

The red spectrum in FIG. 7 is the absorption profile of Alexa Fluor 546, a bi-sulfonated alicyclic xanthene (rhodamine) derivative with a maximum extinction coefficient at 556 nanometers, which is designed specifically to display increased quantum efficiency at significantly reduced levels of photobleaching in fluorescence experiments. The most efficient laser excitation spectral line for Alexa Fluor 546 is the yellow 568-nanometer line from the krypton-argon mixed gas ion laser, which produces an emission efficiency of approximately 84 percent. The next closest laser spectral lines, the 543-nanometer line from the green helium-neon laser and the 594-nanometer lines from the yellow helium-neon laser, excite Alexa Fluor 546 with an efficiency of 43 and 4 percent, respectively.

Instrumentally, and as one skilled in the art will appreciate, fluorescence emission collection of the confocal microscopic imaging system can be optimized by careful selection of objectives, detector aperture dimensions, dichromatic and barrier filters, as well as maintaining the optical train in precise alignment. In most cases, low magnification objectives with a high numerical aperture should be chosen for the most demanding imaging conditions because light collection intensity increases as the fourth power of the numerical aperture, but only decreases as the square of the magnification. However, resolution can be improved with high magnification objectives. Generally, it is appropriate to focus on restrictions imposed by the physical properties of the fluorophores themselves.

The choice of fluorescent probes for confocal microscopy generally should address the specific capabilities of the instrument to excite and detect fluorescence emission in the wavelength regions made available by the laser systems and detectors. Although the current lasers used in confocal microscopy produce discrete lines in the ultraviolet, visible, and near-infrared portions of the spectrum, the location of these spectral lines does not always coincide with absorption maxima of popular fluorophores. In fact, it is not necessary for the laser spectral line to correspond exactly with the fluorophore wavelength of maximum absorption, but the intensity of fluorescence emission is regulated by the fluorophore extinction coefficient at the excitation wavelength (as discussed above). The most popular lasers for confocal microscopy are air-cooled argon and krypton-argon ion lasers, the new blue diode lasers, and a variety of helium-neon systems. Collectively, these lasers are capable of providing excitation at ten to twelve specific wavelengths between about 400 and 650 nanometers.

In a further aspect, the fluorescent dyes for the method and system described herein can be selected based on their molecular weight. Studies have shown that fluorescent dyes having a given molecular weight may not be able to diffuse through particular tissues of interest. For example, Andries and Brutsaert demonstrated that fluorescent dyes that are conjugated to dextran with a molecular weight of 40 kDa did not diffuse through either endocardial endothelium or capillary endothelium, but those with 10 kDa did diffuse easily. Thus, it is desirable to select a molecular weight fluorescent dye that can be introduced and/or diffused into the tissue on interest within a desired time period. See Andries L J, Brutsaert D L. Endocardial endothelium in the rat: junctional organization and permeability. Cell Tissue Res. 1994 September; 277(3):391-400.

In exemplary non-limiting examples, introduction of fluorescent dyes via the formed hydro-gel dye carrier that have a molecular weight of between about 3 to about 10 kDa were quasi instantaneously available for tissue imaging. In various aspects, it is contemplated that the molecular weight of the at least one fluorescent dye can be less than 40 KDa, alternatively, less than 20 KDa, and, optionally, less than 10 KDa.

As exemplarily discussed above, the at least one fluorescent dye can comprise an Alexa Fluor dye. The Alexa Fluor dyes produced by Molecular Probes (Alexa Fluor is a registered trademark of Molecular Probes) are sulfonated rhodamine derivatives that exhibit higher quantum yields for more intense fluorescence emission than spectrally similar probes, and have several additional improved features, including enhanced photostability, absorption spectra matched to common laser lines, pH insensitivity, and a high degree of water solubility. The resistance to photobleaching of Alexa Fluor dyes is high enough that even when subjected to irradiation by high-intensity laser sources, fluorescence intensity generally remains stable for some periods of time even in the absence of antifade reagents. This feature enables the water soluble Alexa Fluor probes to be readily utilized for both live-cell and tissue section investigations, as well as in traditional fixed preparations.

As one skilled in the art will appreciate, the Alexa Fluor dyes are available in a broad range of fluorescence excitation and emission wavelength maxima, ranging from the ultraviolet and deep blue to the near-infrared regions. Alphanumeric names of the individual dyes are associated with the specific excitation laser or arc-discharge lamp spectral lines for which the probes are intended. For example, Alexa Fluor 488 is designed for excitation by the blue 488-nanometer line of the argon or krypton-argon ion lasers, while Alexa Fluor 568 is matched to the 568-nanometer spectral line of the krypton-argon laser. Several of the Alexa Fluor dyes are specifically designed for excitation by either the blue diode laser (405 nanometers), the orange/yellow helium-neon laser (594 nanometers), or the red helium-neon laser (633 nanometers). Other Alexa Fluor dyes are intended for excitation with traditional mercury arc-discharge lamps in the visible (Alexa Fluor 546) or ultraviolet (Alexa Fluor 350, also useful with high-power argon-ion lasers), and solid-state red diode lasers (Alexa Fluor 680). Because of the large number of available excitation and emission wavelengths in the Alexa Fluor series, multiple labeling experiments can often be conducted exclusively with these dyes.

Alexa Fluor dyes are commercially available as reactive intermediates in the form of maleimides, succinimidyl esters, and hydrazides, as well as prepared cytoskeletal probes (conjugated to phalloidin, G-actin, and rabbit skeletal muscle actin) and conjugates to lectin, dextran, streptavidin, avidin, biocytin, and a wide variety of secondary antibodies. In the latter forms, the Alexa Fluor fluorophores provide a broad palette of tools for investigations in immunocytochemistry, neuroscience, and cellular biology. The family of probes has also been extended into a series of dyes having overlapping fluorescence emission maxima targeted at sophisticated confocal microscopy detection systems with spectral imaging and linear unmixing capabilities. For example, Alexa Fluor 488, Alexa Fluor 500, and Alexa Fluor 514 are visually similar in color with bright green fluorescence, but have spectrally distinct emission profiles. In addition, the three fluorochromes can be excited with the 488 or 514-nanometer spectral line from an argon-ion laser and are easily detected with traditional fluorescein filter combinations. In multispectral (x-y-1; referred to as a lambda stack) confocal imaging applications, optical separation software can be employed to differentiate between the similar signals. The overlapping emission spectra of Alexa Fluor 488, 500, and 514 can be segregated into separate channels and differentiated using pseudocolor techniques when the three fluorophores are simultaneously combined in a triple label investigation.

Fluorophores designed to probe the internal environment of living cells have been widely examined by a number of investigators, and many hundreds have been developed to monitor such effects as localized concentrations of alkali and alkaline earth metals, heavy metals (employed biochemically as enzyme cofactors), inorganic ions, thiols and sulfides, nitrite, as well as pH, solvent polarity, and membrane potential. These probes bind to the target ion with a high degree of specificity to produce the measured response and are often referred to as spectrally sensitive indicators. Ionic concentration changes are determined by the application of optical ratio signal analysis to monitor the association equilibrium between the ion and its host. The concentration values derived from this technique are largely independent of instrumental variations and probe concentration fluctuations due to photobleaching, loading parameters, and cell retention.

As noted above, a confocal microscopic imaging system includes a processor that is coupled to a control subsystem and a display, if needed. A memory is coupled to the processor. The memory can be any type of computer memory, and is typically referred to as random access memory "RAM," in which the system software, and image reconstruction software resides. The confocal microscopic imaging system's image reconstruction software controls the acquisition and processing of the received emitted light and allows the confocal microscopic imaging system to display a two-dimensional or three-dimensional confocal image, as desired. In one aspect, the system software and image reconstruction software, can comprise one or more modules to acquire, process, and display data from the confocal microscopic imaging system. The software comprises various modules of machine code which coordinate the confocal microscopic imaging subsystems.

Data is acquired from emitted light of the excited tissue regions of interest. The emitted light can be communicated to the confocal microscopic imaging system via the fiber-optic bundle, where the emitted light is measured and processed to form images, and then, if desired, displayed on a display. The system software and image reconstruction software, allow for the management of multiple acquisition sessions and the saving and loading of data associated with these sessions. Post processing of the image data also enabled through the system software and the image reconstruction software.

As one skilled in the art will appreciate, the confocal microscopic imaging system can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), and the like.

The software of confocal microscopic imaging system comprises executable instructions for implementing control and processing functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory), a digital versatile disc (DVD), and a portable compact disc read-only memory (CDROM). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory can include the image data obtained by the confocal microscopic imaging system and can also include raw data representative of the acquired light. A computer readable storage medium can be coupled to the processor for providing instructions to the processor to instruct and/or configure the processor to perform steps or algorithms related to the operation of the confocal microscopic imaging system. The computer readable medium can include hardware and/or software such as, by way of example only, magnetic disks, magnetic tape, optically readable media such as CD ROM's, and semiconductor memory such as PCMCIA cards. In each case, the media may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The confocal microscopic imaging system can include a control subsystem to direct operation of various components of the confocal microscopic imaging system. The control subsystem and related components may be provided as software for instructing a general or special purpose processor or as specialized electronics in a hardware implementation. The control subsystem is connected to the light source to transmit the desired light at the desired wavelength to the fiber-optic bundle.

The confocal microscopic imaging system includes an image construction subsystem for converting the electrical signals generated by the received emitted light to data that can be manipulated by the processor and that can be rendered into an image. In various exemplary aspects, the imaging system can provide images with a resolution of between about 0.5 µm to 100 µm. The image construction subsystem can be directed by the control subsystem to operate on the received emitted light data to render an image. In a further exemplary aspect, the control subsystem can also comprise a motor control subsystem that is configured to provide a motor control signal to a motor to control the movement of the distal portion of the catheter to a desired a location on the subject.

In one embodiment, a subject is connected to electrocardiogram (ECG) electrodes to obtain a cardiac electrical signal from the subject. In one aspect, the cardiac signal from the electrodes can be transmitted to an ECG amplifier to condition the signal for provision to a confocal microscopic imaging system. It is recognized that a signal processor or other such device can be used instead of an ECG amplifier to condition the signal. If the cardiac signal from the electrodes is suitable as obtained, then use of an amplifier or signal processor could be avoided entirely.

In this aspect, the confocal microscopic imaging system can include an ECG signal processor that, if necessary, is configured to receive signals from an ECG amplifier. The ECG signal processor can be configured to provide signals to the control subsystem. The ECG signal can be used to trigger transmission by the source of light, e.g., a laser, of a single or a number of pulses of light (a pulse train). The confocal microscopic imaging system transmits and receives emitted light data, can provide an interface to a user to control the operational parameters of the confocal microscopic imaging system, and, in an exemplary aspect, can processes data appropriate to formulate an ECG-triggered image.

In one example, the confocal microscopic imaging system detects a trigger signal from the ECG signal processing module. The trigger signal is based on a subject's ECG signal, which is provided to the ECG signal processing module though use of ECG electrodes and, if necessary, the ECG amplifier. The ECG processing module of the confocal microscopic imaging system can be configured to automatically detect for instance the peak of the R-wave, a fixed and repeatable point on the ECG signal trace from which the transmission of raditation therethrough the catheter to the tissue of interest is triggered. Of course, other ECG features or signals of the subject's cardiac activity, such as, for example and without limitation, acoustic signals or measured with ultrasound can also be used to trigger the imaging system. For example, the P-wave, Q-wave, S-wave, and T-wave or features thereof can be used to trigger the light transmission. Each feature referred to above can represent a reference point, which can trigger the image acquisition or provide a marker for selection of images.

In another aspect, it is contemplated that an ECG trace can comprise a first and a second, or more of the above described wave peaks. Each peak can provide a reference point of the ECG signal for triggering transmission of radiation energy. When a peak of a given wave type is selected to trigger the transmission of light, subsequent peaks of the same wave type can be used to trigger subsequent transmissions of light.

In operation, it is contemplated that the distal end portion of the catheter is steered through blood vessels or body cavities to a location adjacent to a tissue of interest. Subsequently, the dye carrier is brought in contact with the desired vessel or cavity surfaces, respectively. After contact of the dye carrier with the surfaces, the florescent dye(s) are allowed to diffuse from the dye carrier into the tissue. The fluorescent dye is then excited by a light source, such as a focused laser beam, of appropriate wavelength to emit light of a different wavelength for transmission through the fiber optics bundle of the catheter. As one will appreciate, scanning through tissue by exciting the dye and measuring intensities of emitted light allows for two- and three-dimensional imaging via a confocal microscopic imaging system.

According to one embodiment, a method for producing an image of a tissue comprises generating light at a desired wavelength, transmitting the light into a fiber-optic bundle toward a distal end of the fiber-optic bundle and through the dye carrier onto a portion of the tissue of the subject that has been introduced with the one or more fluorescent dyes to excite the fluorescent dye therein the selected tissue. Subsequently, emitted light of a different wavelength is emitted by the excited fluorescent dye and is received therethrough the dye carrier and into the distal end of the fiber-optic bundle, which is operatively coupled to a conventional confocal microscopic system. From the measured intensities of emitted light, one-, two- or three-dimensional images of the cardiac tissue are created.

According to another embodiment, a method for producing an ECG-triggered image comprises generating light at a desired wavelength, repeatedly transmitting the light into a subject at a desired location within the subject, wherein a reference point of an ECG signal taken from the subject triggers each sequential light transmission, receiving emitted light emitted from the excited fluorescent dye at the desired location as a result of each light transmission, and processing the received emitted light data to form the confocal image. In one exemplary aspect, a high resolution fast multi-spectral confocal mapping technique and apparatus can be used.

Experimental Data

Figure 8:
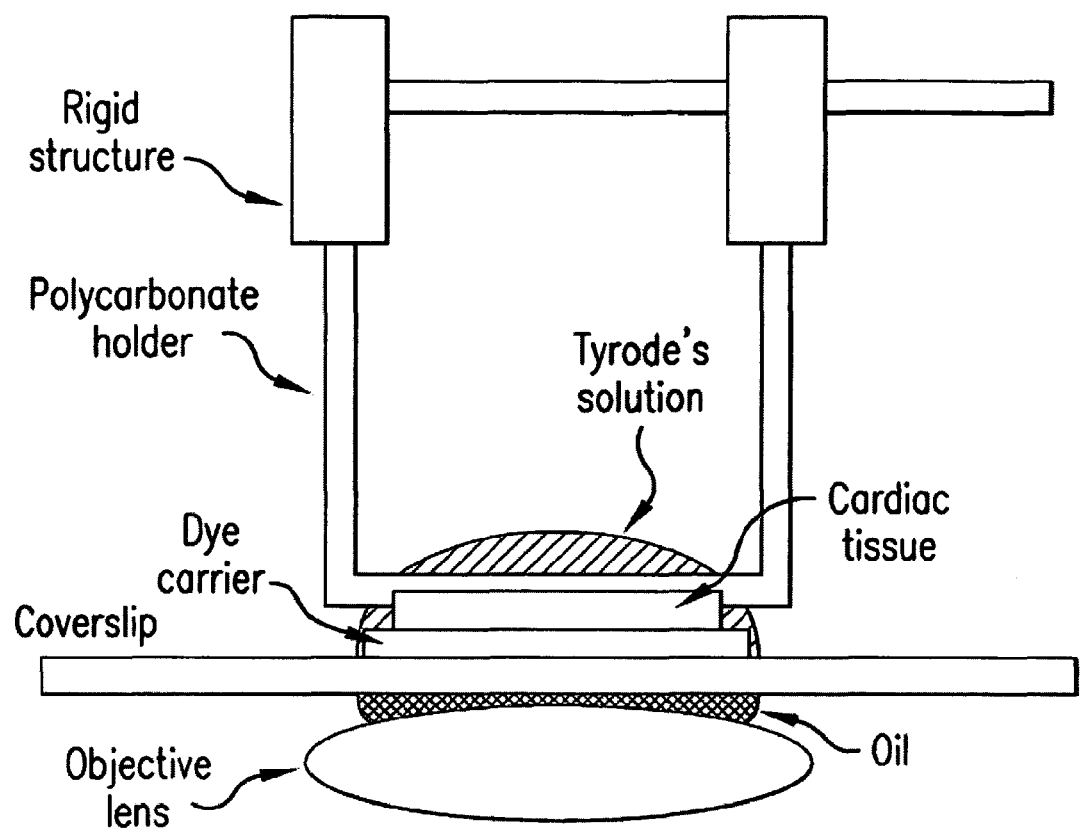
FIG. 8 is an exemplary experimental setup for confocal imaging of cardiac tissue, according to one embodiment.

In one experimental procedure, adult rabbits were anesthetized with pentobarbital (30 mg/kg) and anticoagulated with heparin (2500 USP units/kg). Following thoracotomy, the rabbit hearts were quickly excised and placed in a modified oxygenated Tyrode's solution (in mM: 126 NaCl, 11 Dextrose, 0.1 CaCl2, 13.2 KCl, 1 MgCl2, 12.9 NaOH, 24 HEPES) at room temperature. The hearts were dissected into tissue sections of three types: right ventricular papillary muscle (≈1 mm×1 mm×5 mm), subepicardial ventricular (≈6 mm×2 mm) and atrial tissue (≈6 mm×2 mm). The sections were secured to a polycarbonate holder with sutures as shown in FIG. 8 and stored in the solution until imaging.

The images were obtained within 6 h of heart isolation. Tissue sections were covered by oxygenated Tyrode's solution during the imaging (FIG. 8). Tissue sections were imaged on an 8-bit BioRad MRC-1024 laser-scanning confocal microscope (BioRad, Hercules, Calif.) with a 40× oil-immersion objective lens (Nikon, Tokyo, Japan). Three-dimensional image stacks with a spatial resolution of 200×200×200 nm were obtained with a field of view (X×Y) of 204.8×153.6 μm extending up to 80 μm into the myocardium (Z direction). The Z-axis was substantially parallel to the laser beam direction.

Thin hydrogel slices (4 mm×4 mm×40 μm thick) were created using 6.5% agar (GenePure LE Agarose, ISC BioExpress, Kaysville, Utah) in water. These slices were placed in solutions of fluorescent dyes and the dye was allowed to diffuse into the agar hydrogel. Dextran-conjugated, lysinefixable Texas Red with a molecular weight of 3 kDa and excitation/emission wavelengths of 595/615 nm was used at concentrations of 6-12 mg/mL (Molecular Probes, Eugene, Oreg.). This dye and other dextran-conjugated dyes allow for specific labeling of the extracellular space. An imaging chamber was created by cutting an aperture from the bottom of a polystyrene weighing dish and gluing a size #0 glass slide over the opening. The dye-loaded hydrogel slice was placed on the glass slide and dye was delivered by gently pressing the tissue onto the slide. Precautions were taken to ensure that the tissue sample was not compressed in the imaged region. Image regions with a distance of at least 10 μm between the glass slide and tissue surface were used. As shown in FIG. 8, images were acquired by imaging through the glass slide and hydrogel.

Image stacks were deconvolved with the iterative Richardson-Lucy algorithm using a measured point spread function (PSF). Briefly, the response g of an imaging system to given sources can be described by convolution of the source image f with the point spread function h:

$$g(x) = (f*h)(x) = \iiint_{-\infty}^{\infty} f(x')h(x-x')dx'$$

The iterative Richardson-Lucy algorithm was used to reconstruct the source image f:

$$g_{n+1} = g_n \left( \frac{g_0}{g_n * h} \otimes h \right)$$

with the cross-correlation operator $\otimes$ and $g_0 = g$. The three dimensional PSF was characterized by imaging 100 nm fluorescent beads embedded in agar. Images of fifteen beads were extracted, aligned and averaged to obtain the PSF, which allowed us to quantitatively characterize our imaging approach. Finally, the PSF was filtered by applying an average filter and re-sampled with a resolution of 200 nm×200 nm×200 nm. The PSF was applied to deconvolve the image stacks.

Figure 9:
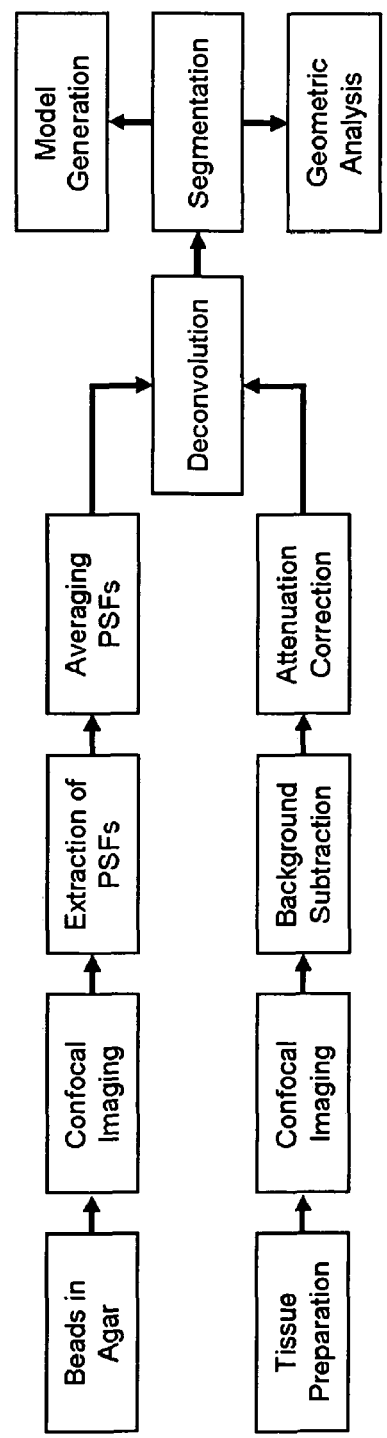
FIG. 9 is a schematic view of an exemplary experimental and processing method for confocal imaging.

Signal-to-noise ratios in the raw images were estimated to characterize image stacks. Regions of 300 voxels were sampled inside myocytes to calculate variances of signal intensity and in the extracellular space to calculate mean signal intensity. The signal-to-noise ratio was calculated from the mean signal intensity divided by the variance. Raw image stacks were processed using a combination of C++ and MatLab software (MathWorks, Natick, Mass.) to remove background signals and correct for depth-dependent attenuation (FIG. 9). The background signal was estimated by averaging signals in small regions where the expected intensity is zero (i.e. inside myocytes). Depth-dependent attenuation of signal intensity was calculated by selecting lines in the Z-axis (laser beam) direction with the smallest standard deviation of the associated intensity. Intensities along these lines were fit to an exponential function using least square optimization to obtain a slice-wise scaling factor as a function of depth.

Figure 13:
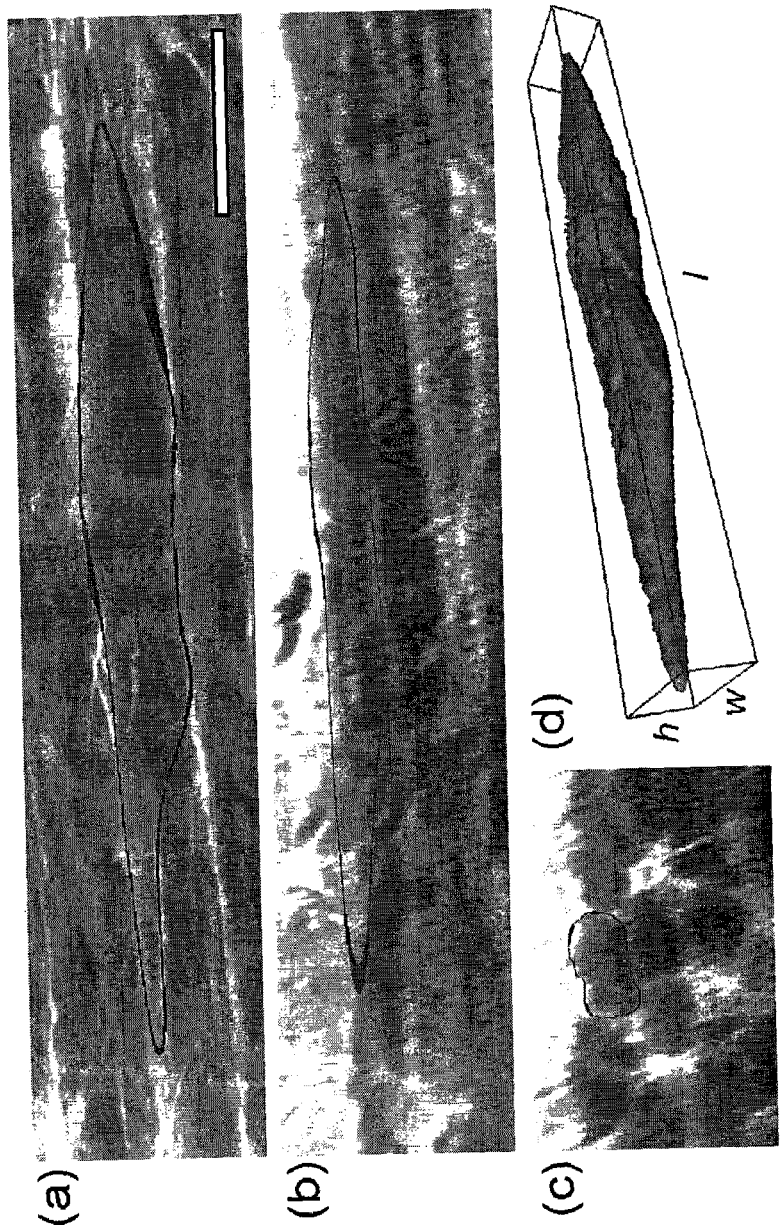
FIG. 13 is exemplary segmentation of a single cardiac myocyte in (a) XY, (b) XZ and (c) YZ images of a trial tissue. Also shown in (d) is a three-dimensional model of myocyte created by manual segmentation and thresholding. Scale: 20 µm applies to (a)-(c).
Figure 14A:
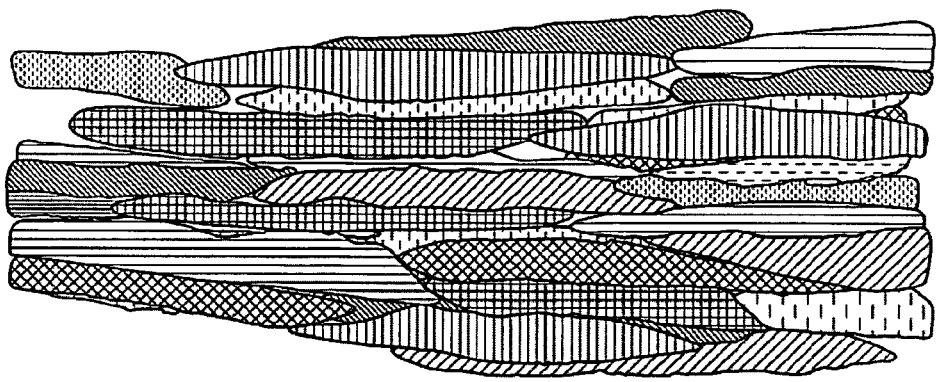
FIG. 14 is a three-dimensional model of a trial tissue shown (a) from epicardial surface, (b) in fiber direction, and (c) from lateral side. Also shown in (d) is a model overlaid with exemplary confocal images in three orthogonal planes. The model includes 17 complete and 21 partial myocytes. Scale: 50 µm applies to (a)-(c).
Figure 14B:
Figure 14C:
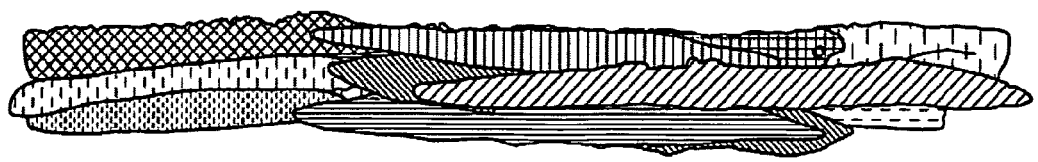
Figure 14D:
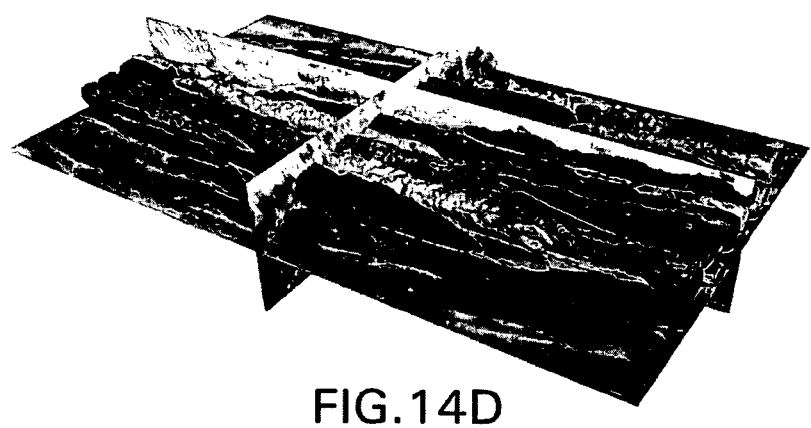

Myocytes were segmented by manually deforming a surface mesh followed by iterative thresholding. As shown in FIG. 13, an initially ellipsoid-shaped mesh comprised of 5120 triangles was wrapped around each myocyte in the field of interest. Histograms of voxel intensities were created for the volume enclosed by each mesh to calculate the mode and standard deviation of voxel intensities. The threshold values were chosen independently for each myocyte based on the calculated mode and standard deviation to distinguish between intra-myocyte and extracellular spaces.

After thresholding, geometric analysis was performed on the extracted whole myocytes. Principal component analysis (PCA) was used to determine the principal axis of each segmented myocyte. A bounding box was created around each myocyte based on the PCA as illustrated in FIG. 13(*d*). The bounding box dimensions in direction of the first, second and third principal axis were considered to be the myocyte length, width and height, respectively. Myocyte volume was calculated by counting the intra-myocyte voxels. Average cross-sectional area was determined by dividing cell volume by length. The volume fraction of tissue occupied by myocytes was determined by sampling random volumes of 300×300×30 voxels within regions of the image stack where all myocytes were segmented. Myocyte density was defined as mean of the myocyte volume fraction (MVF) divided by the volume of each cell (Vi):

$$\text{Myocyte Density} = \frac{1}{n} \sum \frac{MVF}{V_i}$$

Figure 3A:
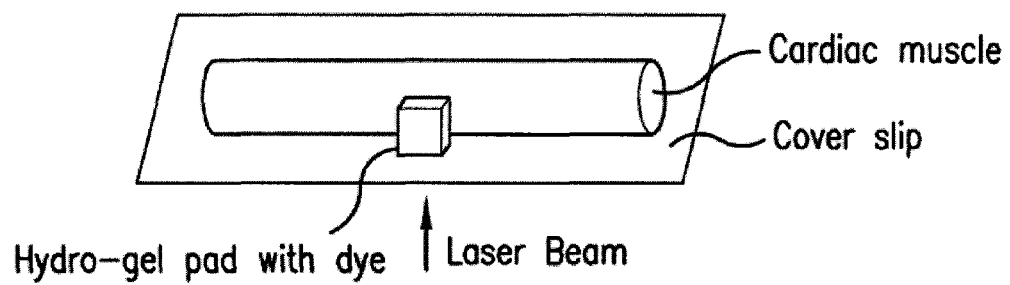
FIG. 3A shows a schematic view of an experimental setup up to study the dynamics of dye diffusion.
Figure 3B:
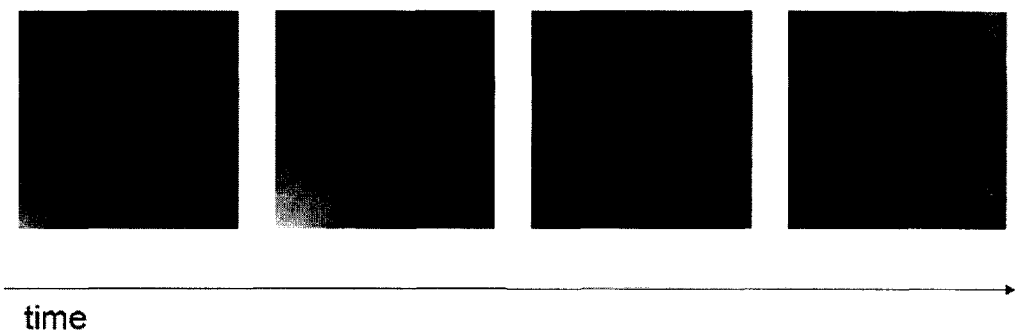
FIG. 3B shows the results from the diffusion study schematically shown in FIG. 3A. In the experimental study, the dye carrier (a hydro-gel pad loaded with fluorescent dye Alexa 488 conjugated to dextran) was brought in contact with the surface of a rabbit papillary muscle. As shown in the time lapsed photographs, diffusion is capable of transporting dye from the carrier into the tissue region of interest. The resulting concentration of dye therein the region of interest is sufficient for confocal imaging.

For some imaging studies, excised hearts were mounted and perfused with the modified Tyrode's solution at 8 mL/min retrogradely through the aorta using the Langendorff method. Two-dimensional images with a field of view of 176.3×124.9 μm and a lateral resolution of 0.48 μm were acquired from the Langendorff preparation with a catheter based confocal system (FCM1000, Leica, Wetzlar, Germany) and a microprobe (M/30). The microprobe tip diameter was 4.2 mm and the working distance was 30 μm. A hydrogel dye carrier was configured as an agar sheath that fit over the catheter tip as shown in FIG. 3(*a*). The dye carrier was brought into contact with the surface of a rabbit papillary muscle. As shown in FIG. 3(*b*), diffusion is capable of transporting dye from the carrier into the tissue region of interest. The resulting concentration of dye within the tissue region of interest was sufficient for confocal imaging.

Figure 11:
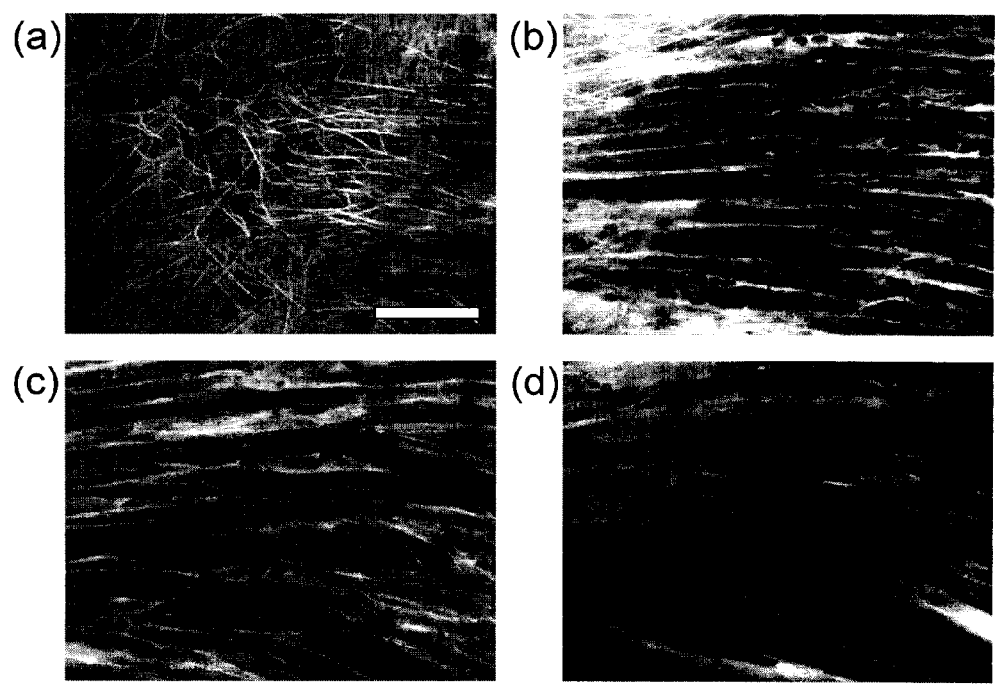
FIG. 11 is exemplary raw XY images from a three-dimensional stack of a trial tissue. The images are from the (a) epicardial surface and a depth of (b) 10 µm, (c) 20 µm, and (d) 30 µm into the myocardium. Scale: 50 µm in (a) applies to (a)-(d).

Upon pressing the tissue sections onto the hydrogel carrier, the dextran-conjugated Texas Red dye diffused rapidly through the endo- or epicardial layers and into the myocardium. The dye was immediately available in sufficient concentration for confocal imaging of the cardiac microstructure. Exemplary two-dimensional images of atrial and ventricular tissue sections acquired with the BioRad confocal microscope are shown in FIGS. 11(*a*) and 12(*d*), respectively. These images originate from three-dimensional stacks covering approximately 1 µm outside of the tissue surface and up to 80 µm into the myocardium.

Fluorescence appeared to be associated with clefts between cells (interstitial space), collagen fibers, transverse tubules and capillary vessels; whereas darker regions appeared to be associated with cells. Image slices through the epicardial and endocardial network of thin collagen fibers in atrial and ventricular tissue are shown in FIGS. 11(*a*) and 12(*a*), respectively. The fibers are brighter than their surroundings and appear to be, to some degree, orientated parallel to the myocytes. The image through the ventricular endocardium (FIG. 12(*a*)) includes endothelial cells.

Figure 4:
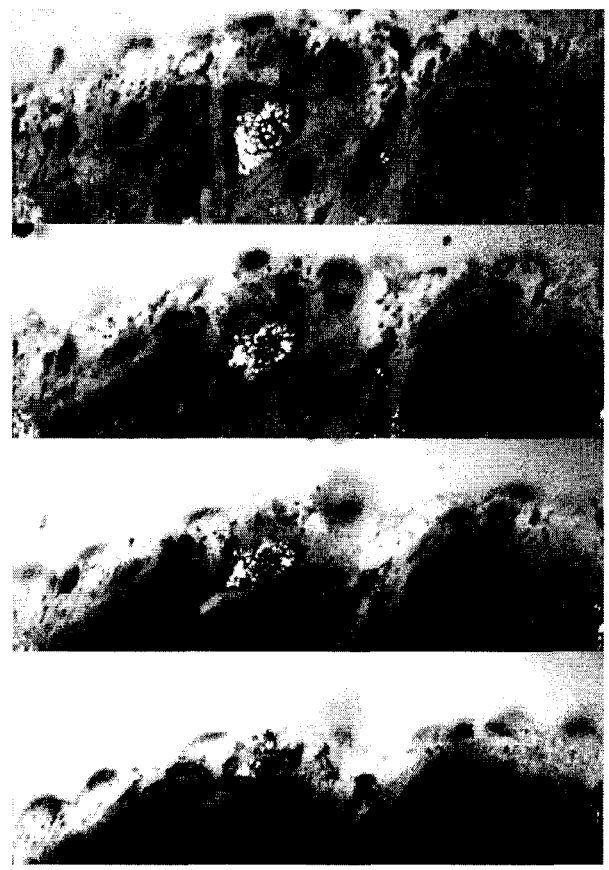
FIG. 4 is a series of confocal microscopic images of tissue microstructure at different depths through a rabbit's left ventricular muscle. In this study, the dye (Alexa 488 conjugated to dextran) penetrated the epicardium and was diffused into the tissue region of interest. Size: 175×44 µm; Pixels: 512× 128; Bits: 8; Depth: ~50 µm; Raw data.
Figure 5:
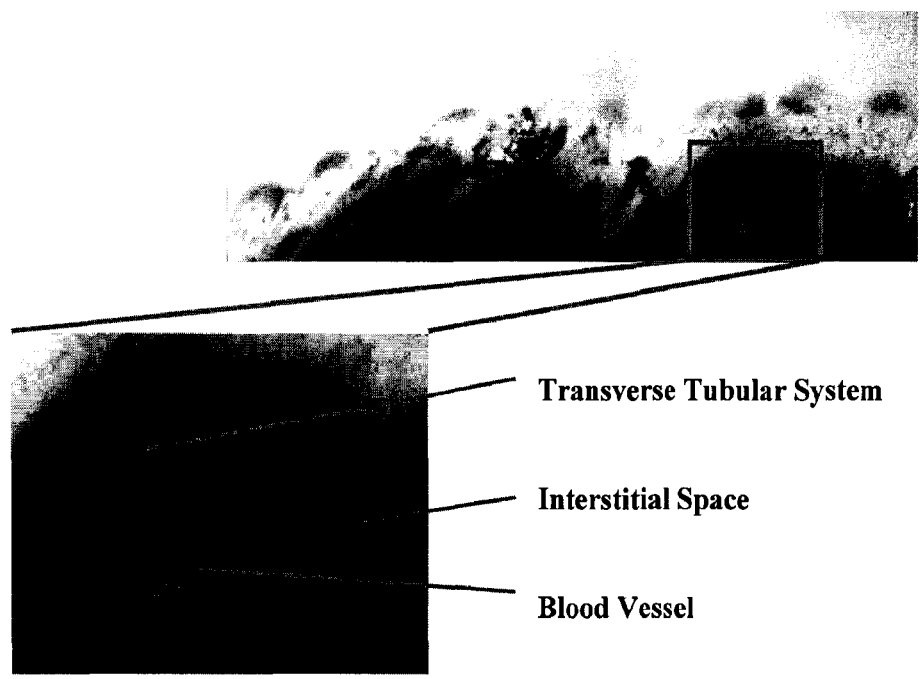
FIG. 5 shows an enlarged portion of a confocal microscopic image from the rabbit's left ventricular muscle. The exemplary images allow for the identification of ventricular myocytes and their transverse tubular system, the interstitial space, and blood vessels.
Figure 6:
FIG. 6 shows an exemplary confocal microscopic image of tissue microstructure of a rabbit papillary muscle. The image is from a stack of 100 images and shows a dense arrangement of myocytes. Size: 236×177 µm; Pixels: 1024×768; Bits: 8; Depth: ~30 µm; Raw data.
Figure 12:
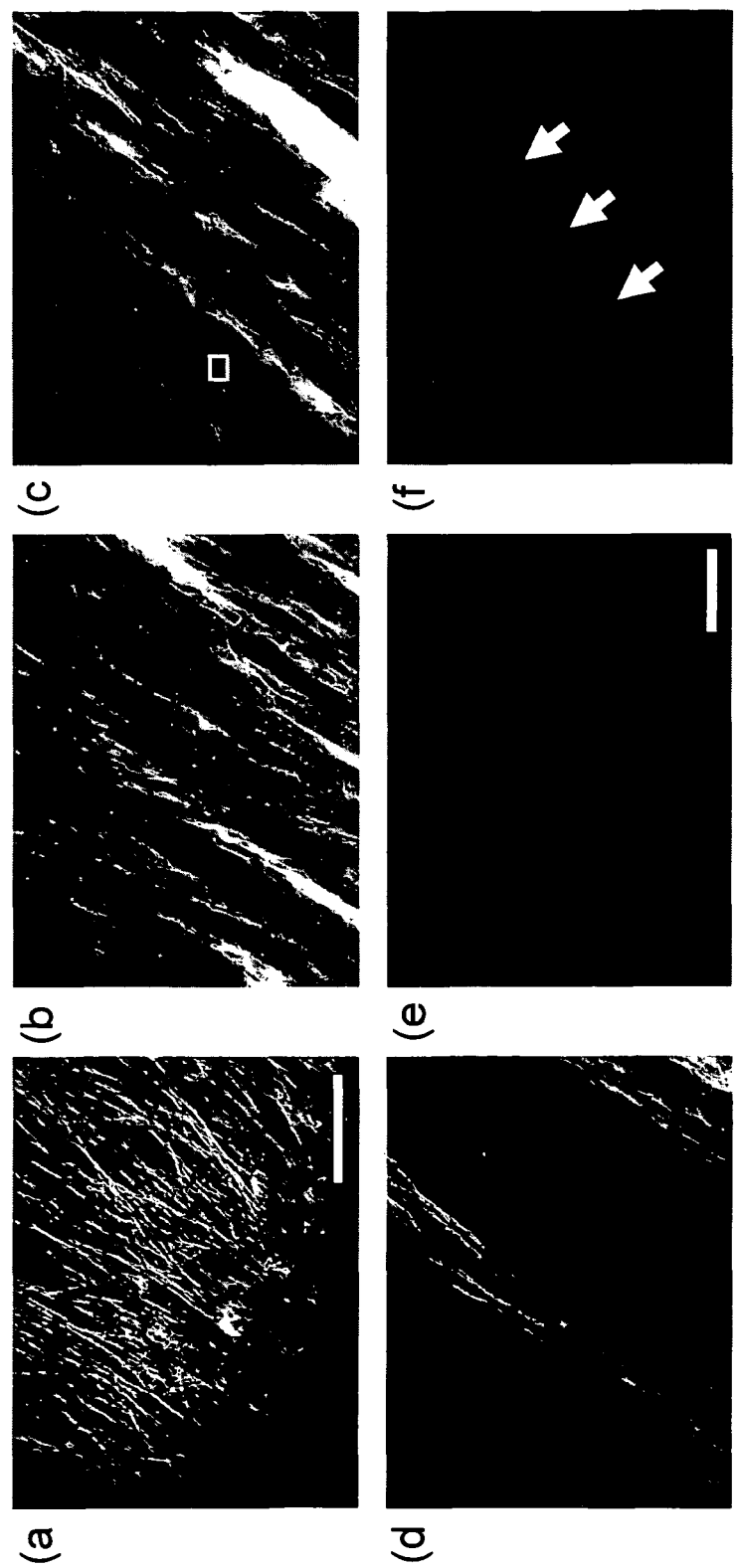
FIG. 12 is exemplary raw XY images from a three-dimensional stack of entricular tissue. The images are from the (a) endocardial surface and a depth of (b) 10 µm, (c) 20 µm, and (d) 30 µm into the myocardium. Also shown are (e) a zoomed view of region marked by white box in (c) and (f) a processed image from region marked by white box in (c). The white arrows indicate cross-sections of transverse tubules. Scales: 50 µm in (a) applies to (a)-(d), 2 µm in (e) applies also to (f).

Image slices into atrial and ventricular myocardium are presented in FIGS. 11(*b*)-(*d*) and FIGS. 12(*b*)-(*d*), respectively. These image slices are from depths of 10, 20 and 30 µm into the myocardium with respect to the epicardial or endocardial surface layer (FIGS. 4 and 5). The density of the network of collagen fibers appeared to be larger in the endo- and epicardium than within the myocardium. Furthermore, images extending further into the myocardium exhibited less overall fluorescence. FIG. 6 shows an exemplary confocal microscopic image of the tissue microstructure of a rabbit papillary muscle. The image was formed from a stack of 100 images. As shown, a dense arrangement of myocytes was visible in the image.

Optical properties of the BioRad confocal microscopy system were characterized by measurement of PSFs as described above. The PSF exhibited full widths at half maximum of 0.30 µm in the XY plane (transverse to the laserbeam) and 1.85 µm in the Z direction (parallel to the laser beam).

Figure 10:
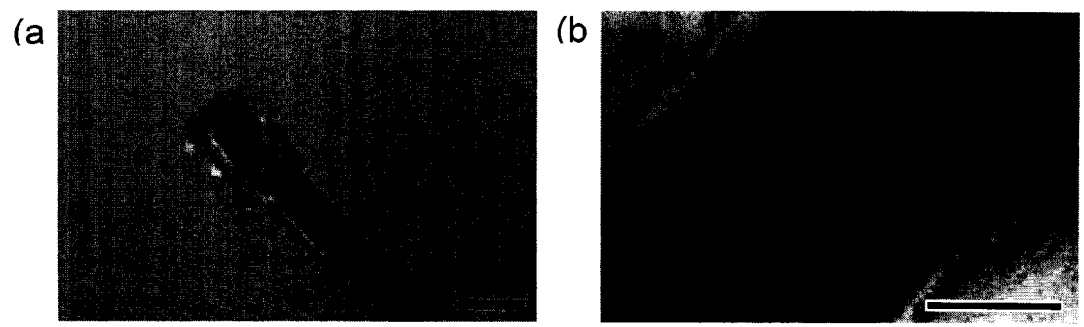
FIG. 10 is an image taken during an exemplary experiment with catheter-based confocal microscopy system (Leica FCM 1000) showing (a) M/30 confocal microprobe with hydrogel carrier loaded with dye; (b) Image of atrial tissue acquired with catheter-based confocal microscopy system and the modified microprobe. Scale: 5 mm in (a) and 50 µm in (b).

In another experiment, images were also acquired with a catheter based confocal microscope (FCM1000, Leica, Wetzlar, Germany). The dye carrier was attached to the catheter tip as shown in FIG. 10(*a*) and gently pressed on the epicardial surface of the atria and ventricles of a Langendorff-perfused heart. An exemplary two-dimensional image of atrial tissue is shown in FIG. 10(*b*). The dye was readily available for imaging. High and low fluorescence intensities were associated with the extra- and intracellular spaces, respectively.

Methods of digital image processing and analysis were applied to quantitatively describe and model cardiac tissue microstructure from three-dimensional image data. For this purpose, 19 image stacks were acquired from a total of 9 rabbits for subsequent analysis. Fourteen of these stacks were rejected from analysis due to low signal-to-noise ratios, discontinuities within the image stack by motion and/or poor tissue quality. Signal-to-noise ratios below 3 were considered low. Background signals were removed, corrected for depth-dependent attenuation, and deconvolved the image stacks. FIGS. 12(*e*) and (*f*) illustrate the effect of this processing on the image stacks. Processed image stacks exhibit fine details of myocytes such as the transverse tubular system (FIG. 12(*f*)), which were difficult to identify in the unprocessed image data (FIG. 12(*e*)).

Figure 15:
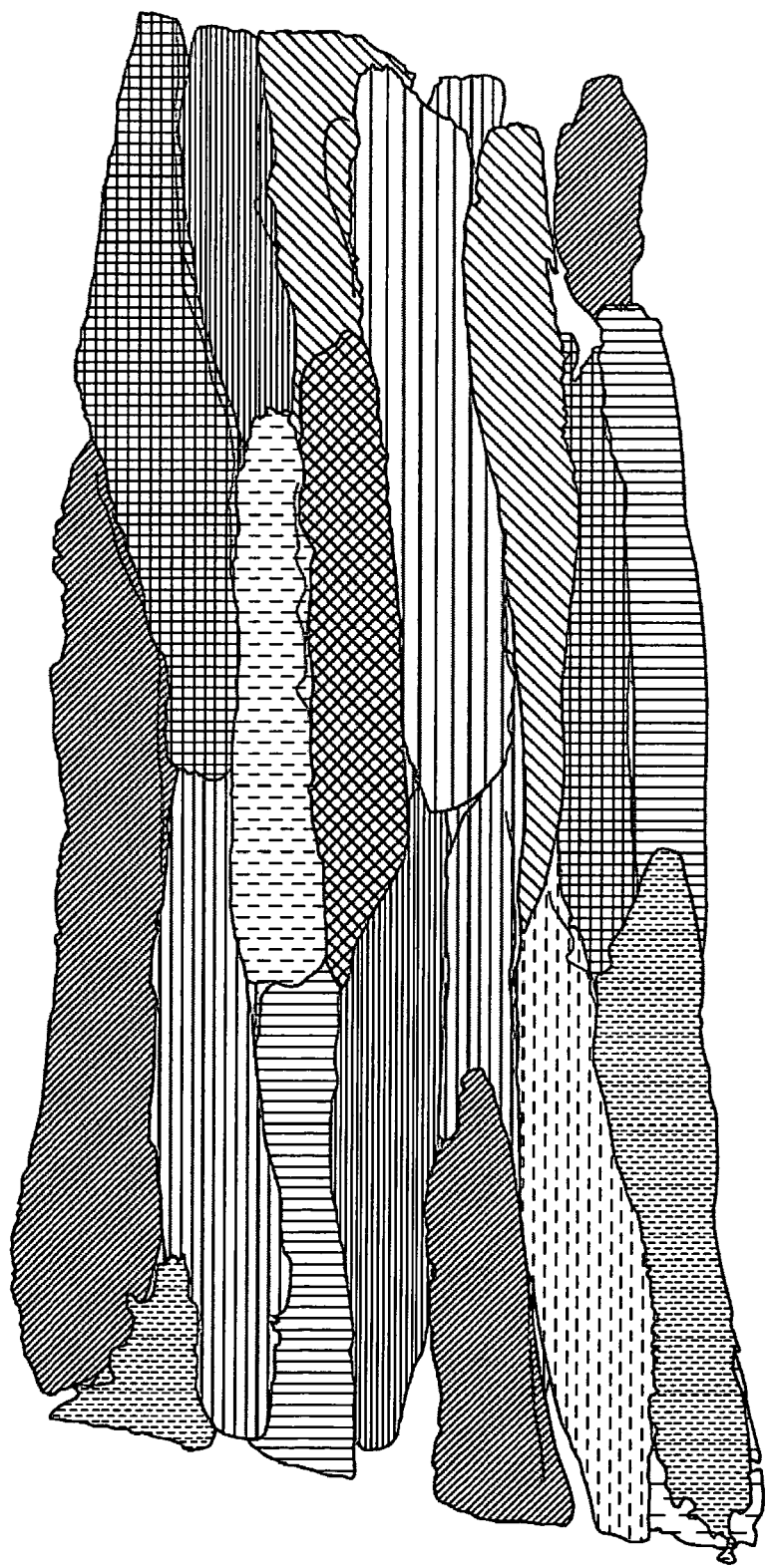
FIG. 15 is a three-dimensional model of ventricular tissue shown from endocardial surface. The model includes 11 complete myocytes and 11 partial myocytes. Scale: 50 µm.

Individual myocytes were segmented from three-dimensional image stacks (FIG. 13), which allowed for subsequent spatial modeling (FIGS. 14 and 15) and quantitative analysis of myocytes (Tables I and II). Segmentation was performed on 50 atrial myocytes and 36 ventricular myocytes. Quantitative analysis was only performed on whole myocytes, which included 28 atrial myocytes and 20 ventricular myocytes.

An exemplary segmentation of a single myocyte from a three-dimensional stack of atrial tissue is shown in FIG. 13. The manually deformed surface mesh is illustrated in three orthogonal planes in FIGS. 13(*a*)-(*c*). Threshold values to distinguish between intra-myocyte and extracellular space were chosen to be the mode plus 2 standard deviations of signal intensity for each segmented myocyte. FIG. 13(*d*) shows the segmented myocyte after thresholding and in a bounding box aligned to the principal axes of the myocyte. The dimensions of the bounding box determined the length, width and height of the myocyte. Three-dimensional spatial models of segmented myocytes from three-dimensional stacks of atrial and ventricular tissue are shown in FIGS. 14(*a*)-(*c*) and 15, respectively. FIG. 14(*d*) shows a three-dimensional visualization of the atrial model overlaid with orthogonal confocal images.

Quantitative analysis revealed mean and standard deviation (mean±sd) of lengths, widths and heights of atrial myocytes to be 105.0±10.6, 13.1±1.7 and 9.7±1.6 µm, respectively, and ventricular myocytes to be 112.3±14.3, 18.4±2.3 and 14.1±2.7 µm, respectively. Average volumes of atrial and ventricular myocytes were 4901±1713 and 10,299±3598 µm$^3$, respectively. Furthermore, the myocyte volume fractions for atrial and ventricular tissue were 72.4±4.7% and 79.7±2.9%, respectively. Myocyte density was 165,571±55,836 and 86,957±32,280 cells/mm$^3$ for atrial and ventricular tissue, respectively. Principal component analysis demonstrated that the long (first principal) axis of myocytes was parallel to the surface of atrial and ventricular tissue (FIGS. 14 and 15) within 6° and 3° deviation to the surface plane, respectively.

Furthermore, the majority of ventricular myocytes (70%) had their second principal axis approximately parallel (<25°) to the tissue surface. In contrast, atrial tissue did not show parallel orientation of the second principal axis with respect to the surface.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

Various publications are referenced in this document. These publications in their entireties are hereby incorporated by reference into this application in order to more fully describe the state of the art to which the disclosed system and method pertains. The references disclosed are also individually and specifically incorporated by reference herein for the material contained in them that is discussed in the sentence in which the reference is relied upon.

What is claimed is:

1. A method for imaging of tissue, comprising:
    operatively coupling a dye carrier to a distal end of a fiber optic bundle, the dye carrier comprising at least one fluorescent dye;
    positioning a portion of the dye carrier in contact with a tissue region of interest of a subject such that at least a portion of the at least one fluorescent dye diffuses into the tissue region of interest; and
    acquiring a confocal image of the tissue region of interest, wherein the step of acquiring the confocal image of the tissue region of interest comprises:

transmitting light into the fiber optic bundle, through the dye carrier, and then into the tissue region of interest to excite the fluorescent dye within the tissue region of interest;

receiving light emitted from the excited fluorescent dye within the tissue region of interest, wherein the light emitted from the excited fluorescent dye is emitted through the dye carrier and then into the fiber optic bundle; and processing the received emitted light to form the confocal image of the tissue region of interest.

2. The method of claim 1, wherein the step of receiving light emitted from the excited fluorescent dye comprises communicating the emitted light to a confocal microscopic imaging system.

3. The method of claim 1, further comprising monitoring an ECG signal taken from the subject, wherein a reference point of the ECG signal taken from the subject triggers the step of acquiring a confocal image of the tissue region of interest.

4. The method of claim 3, wherein the step of monitoring the ECG signal comprises identifying a plurality of sequential reference points of the ECG signal, and wherein the step of acquiring a confocal image of the tissue region of interest is repeated at each sequential reference point of the ECG signal.

5. The method of claim 1, wherein the dye carrier comprises a light transparent matrix.

6. The method of claim 5, wherein the at least one fluorescent dye is at a predetermined concentration.

7. The method of claim 5, wherein the dye carrier comprises at least one antibody agent.

8. The method of claim 5, wherein the light transparent matrix comprises a hydro-gel, and wherein the hydro-gel is configured to permit diffusion of the at least one fluorescent dye from the hydro-gel into the tissue region of interest.

9. The method of claim 8, wherein the light transparent matrix extends from the distal end of the fiber optic bundle by a distance of less than 100 μm.

10. The method of claim 8, wherein the light transparent matrix extends from the distal end of the fiber optic bundle by a distance of less than 200 μm.

11. The method of claim 1, wherein the at least one fluorescent dye is suspended in a buffer solution.

12. The method of claim 11, wherein the at least one fluorescent dye and the buffer solution comprises at least 95% of the dye carrier.

13. The method of claim 1, wherein each fluorescent dye of the at least one fluorescent dye is selected from a group consisting of: Alexa, Texas Red, FITC, Oregon Green, Rhodamine Green, Lucifer yellow, Fluo 3, Fluo 4, and di-8-Anepps.

14. The method of claim 1, wherein each fluorescent dye of the at least one fluorescent dye has a molecular weight of 40 KDa or less.

15. The method of claim 14, wherein each fluorescent dye of the at least one fluorescent dye has a molecular weight of 20 KDa or less.

16. The method of claim 1, wherein each fluorescent dye of the at least one fluorescent dye has a molecular weight of between about 3 KDa and about 10 KDa.

17. The method of claim 1, wherein the tissue region of interest is cardiac tissue.

18. A catheter for developing a confocal image of a tissue region of interest of a subject in a confocal microscopic imaging system comprising a source of light energy that is configured to selectively generate light energy at a desired wavelength, the catheter comprising:

a fiber-optic bundle having a distal end and an opposed proximal end, the proximal end of the fiber-optic bundle being configured for operative communication with the source of light energy of the confocal microscopic imaging system; and a dye carrier coupled to the distal end of the fiber-optic bundle, the dye carrier comprising at least one fluorescent dye, the dye carrier being coupled to the distal end of the fiber-optic bundle such that the dye carrier substantially covers the distal end of the fiber-optic bundle, wherein, upon positioning of a portion of the dye carrier in contact with the tissue region of interest, the dye carrier is configured to permit diffusion of at least a portion of the at least one fluorescent dye into the tissue region of interest, wherein the fiber-optic bundle is configured to transmit the light energy through the dye carrier and then into the tissue region of interest to excite the fluorescent dye within the tissue region of interest.

19. The catheter of claim 18, wherein the dye carrier comprises a light transparent matrix.

20. The catheter of claim 19, wherein the at least one fluorescent dye is suspended in a buffer solution.

21. The catheter of claim 20, wherein the at least one fluorescent dye and the buffer solution comprises at least 95% of the dye carrier.

22. The catheter of claim 19, wherein the at least one fluorescent dye is at a predetermined concentration.

23. The catheter of claim 19, wherein the dye carrier comprises at least one antibody agent.

24. The catheter of claim 19, further comprising a catheter sheath that is configured to selectively and at least partially enclose a distal end portion of the fiber optic bundle.

25. The catheter of claim 24, wherein the catheter sheath is configured to selectively and at least partially enclose at least a portion of the dye carrier.

26. The catheter of claim 18, wherein the at least one fluorescent dye is selected from a group consisting of: Alexa, Texas Red, FITC, Oregon Green, Rhodamine Green, Lucifer yellow, Fluo 3, Fluo 4, and di-8-Anepps.

27. A catheter for developing a confocal image of a tissue region of interest of a subject in a confocal microscopic imaging system comprising a source of light energy that is configured to selectively generate light energy at a desired wavelength, the catheter comprising:

a fiber-optic bundle having a distal end and an opposed proximal end, the proximal end of the fiber-optic bundle being configured for operative communication with the source of light energy of the confocal microscopic imaging system; and a dye carrier coupled to the distal end of the fiber-optic bundle, the dye carrier comprising at least one fluorescent dye and a light transparent matrix, the light transparent matrix comprising a hydro-gel, wherein the hydro-gel is configured to permit diffusion of the at least one fluorescent dye from the hydro-gel into the tissue region of interest at a selected rate, wherein the at least one fluorescent dye is configured to diffuse through the tissue region of interest, and wherein the fiber-optic bundle is configured to transmit light into the tissue region of interest to excite the fluorescent dye within the tissue region of interest.

28. The catheter of claim 27, further comprising a catheter sheath that is configured to selectively and at least partially enclose a distal end portion of the fiber optic bundle.

29. The catheter of claim 28, wherein the catheter sheath is configured to selectively and at least partially enclose at least a portion of the dye carrier.

30. The catheter of claim 27, wherein the dye carrier is coupled to the distal end of the fiber-optic bundle such that the dye carrier substantially covers the distal end of the fiber-optic bundle, wherein the fiber-optic bundle is configured to transmit light through the dye carrier and then into the tissue region of interest to excite the fluorescent dye within the tissue region of interest.

* * * * *

UNITED STATES PATENT AND TRADEMARK OFFICE
CERTIFICATE OF CORRECTION

PATENT NO. : 8,620,409 B2  Page 1 of 1
APPLICATION NO. : 13/057419
DATED : December 31, 2013
INVENTOR(S) : Sachse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 436 days.

Signed and Sealed this
Twenty-second Day of September, 2015

Michelle K. Lee
*Director of the United States Patent and Trademark Office*